US008372408B2

(12) United States Patent
Nizard et al.

(10) Patent No.: US 8,372,408 B2
(45) Date of Patent: Feb. 12, 2013

(54) **USE OF *PHAEODACTYLUM* ALGAE EXTRACT FOR DEPIGMENTING THE SKIN**

(75) Inventors: Carine Nizard, Ivry sur Seine (FR); Marielle Moreau, Marcq (FR); Robin Kurfurst, Saint Jean de Braye (FR); Bertrand Friguet, Paris (FR); Anne-Laure Bulteau, Paris (FR); Monique Gareil, Paris (FR)

(73) Assignee: LVMH Recherche, Saint Jean de Braye (FR)

( * ) Notice: Subject to any disclaimer, the term of this patent is extended or adjusted under 35 U.S.C. 154(b) by 457 days.

(21) Appl. No.: 12/530,266

(22) PCT Filed: Mar. 7, 2008

(86) PCT No.: PCT/FR2008/050394

§ 371 (c)(1), (2), (4) Date: Dec. 7, 2009

(87) PCT Pub. No.: WO2008/125789

PCT Pub. Date: Oct. 23, 2008

(65) Prior Publication Data

US 2010/0092506 A1 Apr. 15, 2010

(30) Foreign Application Priority Data

Mar. 8, 2007 (FR) ..................................... 07 53728

(51) Int. Cl.
*A61K 36/02* (2006.01)

(52) U.S. Cl. .................................. 424/195.17; 424/401

(58) Field of Classification Search ........................ None
See application file for complete search history.

(56) References Cited

U.S. PATENT DOCUMENTS

| | | | | |
|---|---|---|---|---|
| 5,686,489 | A * | 11/1997 | Yu et al. | 514/557 |
| 6,337,320 | B1 * | 1/2002 | Hersh et al. | 514/9.4 |
| 7,220,417 | B2 * | 5/2007 | Nizard et al. | 424/195.17 |
| 2004/0136945 | A1 * | 7/2004 | Nizard et al. | 424/74 |
| 2005/0281869 | A1 * | 12/2005 | Kruse et al. | 424/449 |
| 2007/0042064 | A1 * | 2/2007 | Leverett et al. | 424/777 |
| 2008/0254130 | A1 * | 10/2008 | Gupta | 424/489 |
| 2008/0299147 | A1 * | 12/2008 | Dillon et al. | 424/195.17 |

FOREIGN PATENT DOCUMENTS

| | | |
|---|---|---|
| FR | 2838340 | 10/2003 |
| FR | 2884140 | 10/2006 |
| JP | 1224308 | 9/1989 |
| WO | WO 02-080876 | 10/2002 |
| WO | WO 03-061618 | 7/2003 |
| WO | WO 2006-008401 | 1/2006 |
| WO | WO 2008-125789 | 10/2008 |

OTHER PUBLICATIONS

Friguet et al., "Protein Degredation by the Proteasome and its implication in ageing", Ann. NY Adad. Sci., 2000, 908: 143-154.

Petropoulos et al., "Increase of Oxidatively Modified Protein is Associated with a decrease of proteasome actifity and content in aging epidermal cells", J. Gerontol. A. Biol. Sci., 2000, 55A: B220-227.

Friguiet B., Oxidized Protein degredation and repair in ageing and oxidative stress, FEBS Letters, 2006, 580: 2910-2916.

Ando et al., "In Fatty Acids Regulate Pigmentation via Proteasomal Degradation of Tyrosinase: a new aspect of ubiquitin-proteasom function", J. Biol. Chem, 2004, 279: 15427-33.

* cited by examiner

*Primary Examiner* — Christopher R. Tate
(74) *Attorney, Agent, or Firm* — Woodcock Washburn LLP

(57) ABSTRACT

The invention relates to the use in a cosmetic composition of an extract of the alga *Phaeodactylum tricornutum*, as a depigmenting active agent intended in particular for attenuating or eliminating skin pigmentation marks or for lightening the complexion or bodily hairs or head hair. The extract is preferably a lipid extract. The invention also relates to a cosmetic care method for attenuating or eliminating skin pigmentation marks or for lightening the complexion or bodily hairs or head hair, characterized in that it comprises the application, to at least one concerned area of the skin, of a cosmetic composition containing this extract.

12 Claims, 8 Drawing Sheets

CHYMOTRYPSIN-LIKE ACTIVITY

POST-GLUTAMIC HYDROLASE-LIKE ACTIVITY

TRYPSIN-LIKE

USE OF *PHAEODACTYLUM* ALGAE EXTRACT FOR DEPIGMENTING THE SKIN

CROSS-REFERENCE TO RELATED APPLICATIONS

This application is the National Stage of International Application No. PCT/FR2008/050394 filed Mar. 7, 2008, which claims the benefit of French Patent Application No. 0753728 filed Mar. 8, 2007, the disclosures of which are incorporated herein by reference in their entireties.

TECHNICAL FIELD

The present invention relates to the use of an extract of the alga *Phaeodactylum tricornutum* as a depigmenting cosmetic agent, and also to a cosmetic skincare method for attenuating or eliminating pigmentation marks or for lightening the complexion, bodily hairs or head hair.

BACKGROUND

Many depigmenting agents are known in the prior art. Proteasome is an intracellular multi-enzyme proteolytic complex that is very important in cell maintenance since it is in charge especially of removing damaged proteins (Friguet B. et al., Protein degradation by the proteasome and its implication in ageing, Ann. NY Acad. Sci. (2000) 908: 143-154). The proteasomal system is formed from a catalytic complex, the proteasome 20S and several regulators that influence its activity and its specificity. Association of the regulator 19S with the proteasome 20S forms the proteasome 26S, which performs the degradation of ubiquitin proteins. The proteasome is located in mammalian cells both in the cytosol and the nucleus, and interactions exist with the endoplasmic reticulum and the cell membrane. The proteasome 20S has a molecular mass of 700 kDa and is composed of 14 different subunits encoded by genes either of a type or of β type. The 14 subunits are arranged as a cylindrical stack of four rings of seven subunits, the apical rings being formed from α subunits and the central rings from 13 subunits. This proteolytic complex preferentially cleaves the proteins at the C-terminal end of basic residues ("trypsin-like" activity), hydrophobic residues ("chymotrypsin-like" activity) and acidic residues ("peptidylglutamyl-peptide hydrolase" activity). These peptidase activities are borne by three different β subunits and are located within the structure, thus avoiding the untimely degradation of cell proteins, but posing the problem of accessibility of the active sites to their potential substrates. Finally, during the course of cell ageing, an accumulation of damaged proteins bearing carbonyl groups takes place, which is the signature of modifications of the amino acids by oxidation, which is at least partly explained by a reduction in proteasome activity (Petropoulos, I. et al., Increase of oxidatively modified protein is associated with a decrease of proteasome activity and content in aging epidermal cells. J. Gerontol. A. Biol. Sci. (2000) 55A: B220-227 and Friguet B., Oxidized protein degradation and repair in ageing and oxidative stress, FEBS Letters (2006) 580: 2910-2916).

Moreover, Ando H. et al., in Fatty acids regulate pigmentation via proteasomal degradation of tyrosinase: a new aspect of ubiquitin-proteasome function. J. Biol. Chem. (2004). 279: 15427-33, have demonstrated that, in B16F10 cells (murine melanocyte line that stably expresses and produces melanin), tyrosinase is degraded via proteasome-dependent proteolysis and that this degradation may be stimulated after treatment with linoleic acid or, on the contrary, reduced via treatment with palmitic acid.

The alga *Phaeodactylum tricornutum* is a diatomaceous unicellular alga that forms part of phytoplankton and that originates from temperate climes.

International patent application WO 02/080 876 in the name of the Applicant discloses the use of an extract of this alga as a cosmetic agent for actively protecting the skin against the harmful effects of exposure to UV or for preventing or retarding the effects of ageing of the skin.

According to said international patent application, the properties of this cosmetic agent are explained by the fact that this extract promotes activation of the proteasome of skin cells, in particular of keratinocytes, thus leading toward promoting the degradation of the oxidized proteins.

A process for preparing a clarified culture medium of at least one photosynthetic marine and/or freshwater microorganism and the use of this clarified culture medium especially in the field of cosmetics has also been described in international patent application WO 2006/008 401.

Although said document mentions, among the possible applications of the clarified culture media, applications as either pigmenting agent or depigmenting agent, it in no way concerns the use of the biomass in itself or of its extracts. What is more, it indicates that the clarified matter of the alga *Phaedodactylum tricornutum* does not have any depigmenting properties.

It is recalled that the mechanism of formation of skin pigmentation involves the synthesis of melanin in the melanocytes. This mechanism schematically involves the following main steps:

Tyrosine→Dopa→Dopaquinone→Dopachrome→Melanin

Tyrosinase is an enzyme that plays an essential role in this sequence of reactions. The tyrosinase especially catalyzes the reaction for the conversion of tyrosine into dopa (dihydroxyphenylalanine) and the reaction for the conversion of dopa into dopaquinone leading to the formation of melanin pigments.

A substance is acknowledged as being a depigmenting agent if it acts directly on melanocytes by inhibiting the activity of these cells or if it blocks one of the steps of melanin biosynthesis. This is the case especially when the substance under consideration inhibits one of the enzymes involved in melanogenesis.

BRIEF DESCRIPTION OF THE DRAWINGS

The figures are given with reference to the tests presented in section II of the examples. They illustrate, respectively, comparatively.

DETAILED DESCRIPTION OF ILLUSTRATIVE EMBODIMENTS

Figure 1A:
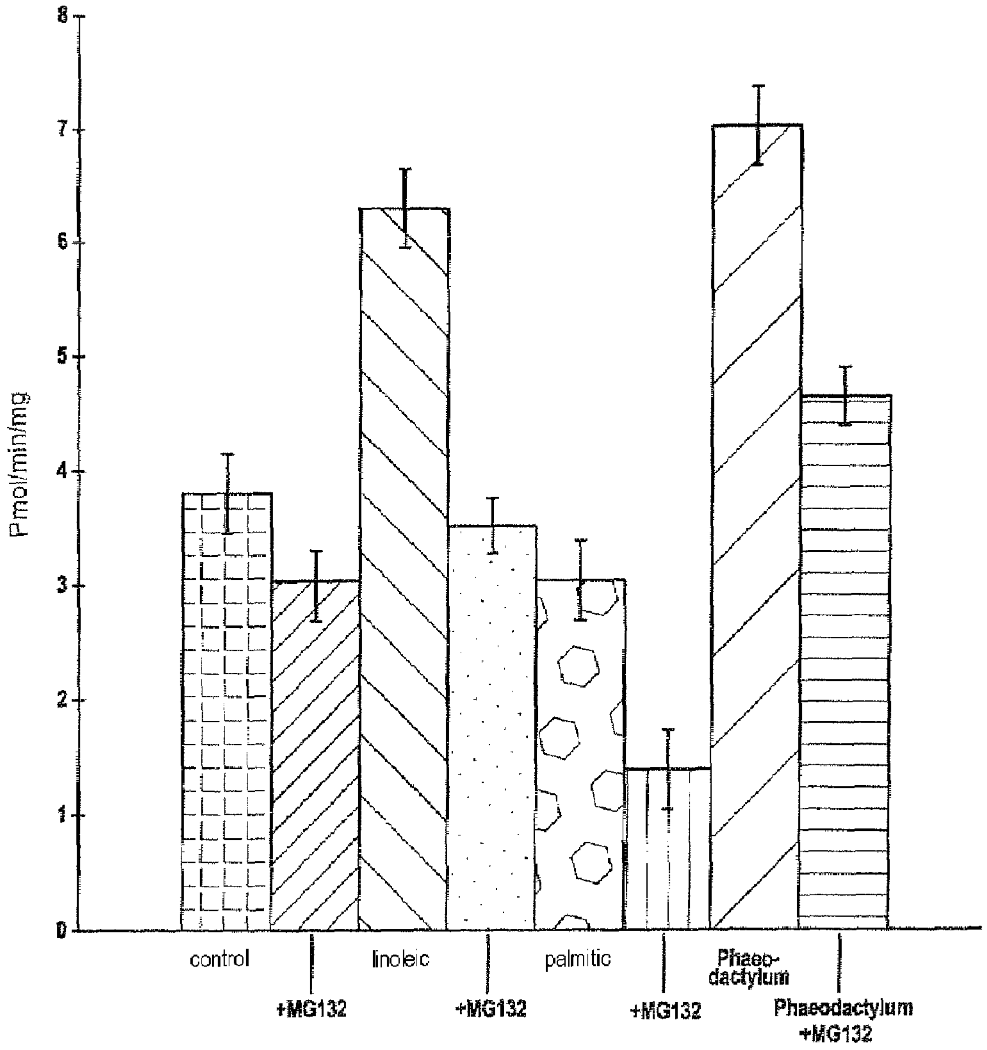
FIG. 1A: the chymotrypsin-like activity.

Surprisingly, the inventors have demonstrated that extracts of the alga *Phaeodactylum tricornutum* have noteworthy skin-depigmenting properties, whereas this same alga is reputed for containing substantial amounts of palmitic acid, which is known according to the scientific publication cited hereinabove (Ando et al., J. Biol. Chem. (2004) 279, 15427-33), for its inhibitory activity on tyrosinase degradation.

Thus, according to a first aspect, the invention relates to the use in a cosmetic composition of an extract of the alga *Phaeodactylum tricornutum*, as a depigmenting active agent intended in particular for attenuating or eliminating skin pigmentation marks or for lightening the complexion, bodily hairs or head hair.

According to this first aspect, the invention relates more particularly to the use in which the active agent is intended for depigmenting or bleaching the skin.

According to a second aspect, the invention relates to a cosmetic care method for attenuating or eliminating skin pigmentation marks or for lightening the complexion, bodily hairs or head hair, characterized in that it comprises the application to at least one concerned area of the skin of a cosmetic composition containing this extract.

According to this second aspect, the extract is used in an amount that is effective to obtain the desired effect, and, in particular, to induce stimulation of tyrosinase degradation in the skin.

In the above two aspects, the algal extract is used in the composition at a concentration preferably of between 0.001% and 5% by weight and even more preferentially between 0.001% and 1% by weight.

The tests performed by the inventors of the present invention have shown that the extract is proportionately more active the higher its fatty acid content.

This is why an extract of *Phaeodactylum tricornutum* that is as rich as possible in fatty acids, and preferably an extract containing at least 40% by weight and preferably at least 60% by weight of fatty acids, will be used according to each of the two aspects of the invention.

A process for obtaining a fat-rich extract may be used to obtain such an extract.

According to a first variant, in order to obtain a fat-rich extract, a process comprising at least one step of extraction with a solvent or solvent medium that is sufficiently apolar to extract fatty acids will be used.

Such a solvent or solvent medium will be referred to hereinbelow as an apolar solvent.

Examples of such apolar solvents that will be mentioned include isopropanol, hexane, cyclohexane and heptane.

However, it is advantageous not to be limited to such a step of treatment of the alga with an apolar solvent, but to use in many cases a sequence of extraction steps, among which is, in addition to the step of extraction with an apolar solvent, at least one step of extraction with a polar solvent.

The result of such an extraction step with a polar solvent is to cause the hydrolysis of esterified fatty acids, in particular glycerides, and to extract them in the form of salts.

Advantageously, such a process comprising at least one step of extraction with an apolar solvent in particular comprises at least one step of extraction with an extraction solvent chosen from $C_1$-$C_6$ alcohols, aqueous-alcoholic or mixtures of these alcohols, $C_2$-$C_6$ polyalcohols such as ethylene glycol, chlorinated solvents such as chloroform and dichloromethane, $C_3$-$C_6$ organic acid esters such as ethyl acetate, $C_6$-$C_{10}$ alkanes such as heptane, hexane or cyclohexane, and $C_5$-$C_8$ ethers such as diisopropyl ether, the said solvent optionally being basified.

According to one particularly advantageous variant of the process used for preparing the extract of the invention, the alga is subjected to a first step of extraction with a basified aqueous-alcoholic mixture, the alcohol of said aqueous-alcoholic mixture preferably being chosen from isopropanol, ethanol and methanol, said step allowing the fatty acids to be recovered in salified form in the aqueous-alcoholic phase.

According to one particularly advantageous variant of the above process according to which the alga is treated in a first step with a basified aqueous-alcoholic mixture, the fraction thus recovered is subjected to various operations aimed at recovering in an apolar phase an extract that is particularly enriched in fatty acids.

In particular, the basified aqueous-alcoholic mixture is acidified before subjecting it to a liquid/liquid extraction step using an apolar solvent.

Such a process also includes a step of recovering an oil containing said extract by removal of said apolar solvent.

This apolar solvent will advantageously be heptane, hexane or cyclohexane.

In general, before any extraction operation, the alga is advantageously frozen. Preferably, the freezing is performed at a temperature between −40° C. and −20° C. approximately and for a time preferably of between 1 and 7 days approximately. This preliminary step is advantageously used to create a heat shock by contact with the future extraction solvent in order to facilitate the decantation of the silica (derived from the skeleton of the algal cells). The alga is then placed in contact with the extraction solution.

According to one advantageous embodiment variant, the frozen alga is immersed directly in the heated extraction solvent.

Maceration of the alga in the extraction solvent at room temperature is also advantageously performed.

According to one advantageous embodiment variant, maceration of the alga is performed at room temperature and preferably for a time of between 5 minutes and 80 minutes approximately and more preferably for a time of between 20 minutes and 40 minutes approximately.

According to yet another advantageous embodiment variant, the extraction is performed at reflux.

According to yet another advantageous embodiment variant, the extraction may be performed under an inert atmosphere, preferably under a nitrogen-saturated atmosphere. This makes it possible in particular to avoid pronounced oxidative degradation of the active molecules.

This extract is advantageously conditioned under an inert gas such as nitrogen, antioxidants also possibly being added in order to protect the active molecules.

According to one advantageous embodiment variant, the amount of extraction solvent used is between 0.1 liter and 20 liters approximately and preferably between 2 liters and 10 liters approximately, for an amount of 100 g of the alga, expressed as dry weight of alga.

According to another advantageous variant of the process in which the extraction step with an apolar solvent is preceded by an extraction with a basified aqueous-alcoholic mixture, the extract of the abovementioned alga is obtained after the following sequence of steps, some of which are described hereinabove:

a) the alga is frozen as described previously and then immersed in the extraction solvent, b) maceration of the alga is performed, c) the extraction solvent is basified to a pH of between 10 and 14, preferably to a pH equal to 13, for example with an aqueous sodium hydroxide solution or with an aqueous potassium hydroxide solution, d) the insoluble matter is removed from the aqueous-alcoholic phase, e) distilled water is added to the aqueous-alcoholic phase, f) the aqueous-alcoholic solution thus obtained is washed via a liquid/liquid process with an apolar solvent that is immiscible with the aqueous-alcoholic phase, for instance heptane, hexane or cyclohexane, g) the phase containing the apolar solvent is removed, h) the aqueous-alcoholic phase recovered after removal of the phase containing the apolar solvent is acidified to a pH of between 1 and 3, preferably to a pH equal to 2, for example with an aqueous sulfuric acid solution or with an aqueous hydrochloric acid solution, i) the solution obtained after acidification undergoes a liquid-liquid extraction with an apolar solvent that is immiscible with the alcoholic or aqueous-alcoholic phase, for instance heptane, hexane or cyclohexane, j) the aqueous-alcoholic phase is then removed, k) the phase containing the apolar solvent recovered after removal of the aqueous-alcoholic phase undergoes an evaporation in order to obtain an oil free of apolar solvent, this oil being the extract desired according to the invention.

The use of a basified and then acidified alcohol makes it possible to obtain an extract with visual and olfactory characteristics that are acceptable in cosmetic compositions (yellow color, and acceptable odor).

According to a second advantageous embodiment of the invention, the abovementioned algal extract is obtained by extracting the alga with supercritical $CO_2$. The use of this particular solvent implies that the alga has been freeze-dried beforehand.

Other characteristics, aims and advantages of the present invention will emerge clearly in the light of the explicative description that follows, given with reference to several implementation examples of the invention, and to comparative activity tests, and examples of formulation of cosmetic compositions, given purely as illustrations that shall not in any way limit the scope of the invention.

In the examples, unless otherwise indicated, the proportions given are expressed as weight percentages. The temperature is in degrees Celsius and the pressure is atmospheric pressure.

EXAMPLES

I. Preparation of Extracts According to the Invention

Example 1

Extraction with a Polar Solvent, Such as Isopropanol (IPA), According to a First Process According to the preferred mode of the process, the entire extraction is performed under an inert atmosphere (saturation with nitrogen) in order to avoid pronounced degradation of the active molecules.

In this example, 250 kg of biomass (*Phaeodactylum tricornutum*) are used.

This biomass, which is frozen at −20° C., is then dipped into isopropanol (IPA) brought to reflux at 80-83° C., with stirring. The heat shock facilitates the decantation of the silica (derived from the skeleton of the algal cells).

The amount of solvent used is 10 liters of IPA per 1 liter of water contained in the biomass. Thus, for a percentage of solids of 30%, the abovementioned 250 kg of biomass are divided up as follows in an amount of solids of 75 kg and 175 kg of water. The amount of IPA used is in this case 1750 kg.

The whole (biomass+IPA) is refluxed for 30 minutes with stirring at about 80° C., and then cooled to about 50° C. After cooling the biomass and the IPA to about 50° C., the whole is transferred into a filter of Guedu type in order to perform the separation of depleted biomass/algal extract dissolved in IPA.

The extract is concentrated in a batch reactor (concentration factor=71.5). The concentrated extract has an oily appearance.

This oily extract is then taken up in cold IPA at a rate of 10 kg of solvent per 1 kg of oil. Stirring is continued for 20 minutes. The liquor is then filtered (which allows the residual tacky sludge to be removed).

A decolorization and deodorization treatment is performed in two batches in an 80-liter Schott reactor, and lasts 30 minutes at room temperature by addition of zeolite and active charcoal. The amount of zeolite (Absent 2000, supplier UOP) added is 0.94 kg and that of active charcoal (CXV, supplier CECA) is 1.6 kg. The charcoal-to-zeolite ratio is 1.7.

The zeolite and the charcoal are then removed by filtration through paper.

Antioxidants (DL-α-tocopherol at a final weight concentration of 0.05% and ascorbyl palmitate at a final weight concentration of 0.05%) are incorporated via a stock solution in IPA.

The filtrate containing the antioxidants is then concentrated batchwise, under an inert gas such as nitrogen, until a brown-colored oil is obtained.

This oil will be referred to hereinbelow as: extract E1 according to the invention of the alga *Phaeodactylum tricornutum*.

Example 2

Extraction According to a Second Process in Two Steps

The extraction starts by dispersing 49.8 kg of frozen dry mass derived from 250 kg of biomass (*Phaeodactylum tricornutum*), i.e. about 20% of dry mass in 539 kg of anhydrous 96% ethanol, basified with 9 kg of aqueous 30.5% sodium hydroxide solution. After maceration for 30 minutes at the reflux temperature of the ethanol and under a nitrogen atmosphere, the whole is cooled to 18° C.

The insoluble matter is then separated out by suction filtration under nitrogen and is discarded.

151 kg of distilled water are added to the 573.9 kg of filtrate. This aqueous-alcoholic phase is stirred slowly for 10 minutes and then washed by means of a liquid/liquid process with 162 kg of heptane. The heptane epiphase of the liquid/liquid partition is removed. The hypophase is recovered since it contains the fatty acids in saline form, as a result of the basification performed at the start of the extraction. The heptane-washing operation is repeated twice more and the hypophase is systematically recovered.

The 720 kg of hypophase thus obtained are acidified by adding 2.8 kg of sulfuric acid to bring the pH to a value of 2.2 and thus to obtain the fatty acids in acid form. The whole solution is stirred for 10 minutes under nitrogen and then subjected to liquid/liquid extraction with an apolar solvent, said apolar solvent being formed in this case by a fraction of 158 kg of heptane. The heptane-washing operation is repeated five times more to recover in total 697 kg of heptane phase obtained from the five fractions containing the free fatty acids. This phase, evaporated to dryness on a rotary evaporator and then by molecular distillation, gives the active extract according to the invention, i.e. an amount representing 0.65 kg of oil.

The oil produced is a homogeneous liquid and has a dark yellow color.

This oil will be referred to hereinbelow as extract E2 according to the invention of the alga *Phaeodactylum tricornutum.*

The extract E2 as obtained according to the abovementioned process has the following fatty acid composition (weight percentage):

| | |
|---|---|
| myristic acid | 4.16% |
| palmitic acid | 13.82% |
| palmitoleic acid | 16.48% |
| eicosapentaenoic acid | 24.75% |
| docosahexaenoic acid | 1.75% |

II. Tests to Demonstrate the Activity of the Extract of the Invention on Melanocyte Proteasome and on the Tyrosinase Activity of these Melanocytes 1. Test Principles The tests described below are aimed at characterizing the influence of the extract of the invention on the various activities of melanocyte proteasome, by measuring the various activities of this proteasome.

They are also aimed at characterizing the influence of the extract of the invention on the amount of ubiquitin proteins.

They are also aimed at characterizing the effects of the extracts of the invention on the amount of tyrosinase and on its activity.

All the tests described in this section were performed using the extract E2 prepared according to Example 2 above.

2. Materials and Methods 2.1 Treatment of MNT1 Cells (Human Melanocyte Cell Lines) in Order to Assay the Proteasome and Tyrosinase Activities 2.1A: Cell Culture The reagents used are defined hereinbelow in the text.

a) Protocol Followed

Inoculation on D0

MNT1, $10^6$ cells/dish 35 mm in diameter, in triplicate

MNT1 culture medium, 2 ml/dish (see composition below)

Treatment on D1

Linoleic acid 25 μM

Palmitic acid 25 μM

*Phaeodactylum* 5 μg/ml in MNT1 medium

+1% BSA+Vitamin E 50 μM+Vitamin C 1 mM

Linoleic acid 25 μM

Palmitic acid 25 μM

*Phaeodactylum* 5 μg/ml in MNT1 medium

+1% BSA (bovine serum albumin)+Vitamin E 50 μM+Vitamin C 1 mM

Stirring with a magnetic bar at 37° C. for 1 hour $2^{nd}$ treatment on D4

+Cycloheximide 1 μg/ml (protein synthesis inhibitor)

+120 nM Mg132 for the assay of the tyrosinase activity.

Preparation of the lyzates after 4 hours 2 rinses with PBS (phosphate-buffered saline)

On a bed of ice; recovery in 150 μl of lysis buffer by scraping.

Freezing at ±20° C.

Protein assay via the Bradford method

Proteasome activity assay b) Media and Reagents

MNT1 Culture Medium

DMEM 4.5 g/ml of glucose (Gibco: 61965-026)

+20% FCS

+10% supplement AIMV (Gibco: 12055-091)

+1% Sodium pyruvate 100 mM (Gibco: 12360-039)

+1% non-essential amino acids, NEAA (Gibco: 11140-035)

Stock Solutions

Linoleic acid (Sigma; L1012)

2.8 mg/ml in EtOH (0.25% in medium)

Palmitic acid (Sigma; P5585)

2.56 mg/ml in EtOH (0.25% in medium)

*Phaeodactylum*

2 mg/ml in EtOH (0.25% in medium)

Vitamin C 25.6 mg/ml in PBS (1% in medium)

Vitamin E 21.55 mg/ml in EtOH (0.1% in medium)

Mg 132 (Sigma; C2211)

120 μM in DMSO (0.1% in medium)

Cycloheximide (Sigma; C7698)

Lysis Buffer

Tris-HCl 1.5 M, pH 7.5

45.375 g of Tris base (Sigma; $T150_3$) to be dissolved in 200 ml of distilled water, adjust the pH to 7.5 with 12N HCl and then make up to 250 ml 1M sucrose solution (Merck; ref 7654)

8.55 g to be dissolved in 20 ml of distilled water, and then adjust to 25 ml.

2 mM $MgSO_4$ solution (Sigma; ref. M7506)

6 mg to be dissolved in 25 ml of distilled water.

Or $MgSO_4.7H_2O$ (Sigma; ref. M5921) 12.4 mg to be dissolved in 25 ml of distilled water;

store at 4° C.

4% Triton X100 solution (Sigma; ref. X100)

0.8 g to be dissolved in 20 ml of distilled water (very slow)

Take a 0.5 ml aliquot and store at −20° C.

40 mM PMSF solution (Sigma; ref. P7626)

14 mg to be dissolved in 2 ml of absolute ethanol.

Take a 50 ml aliquot and store at 4° C., for 9 months 0.5 mg/ml leupeptin solution (Sigma; ref. L2884; stored at −20° C.)

Water-soluble. Take a 50 μl aliquot and store at −20° C., for 1 month.

1M DL-dithiothreitol solution (Sigma; ref. D0632 stored at 4° C.)

0.154 g to be dissolved in 1 ml of distilled water.

Take a 10 μl aliquot and store at −20° C.

500 mM tetrasodium EDTA solution (Sigma; ref. ED4S)

3.8 g to be dissolved in 20 ml of distilled water; stored at 4° C.

Preparation of the Lysis Buffer (per 100 ml)

Preparation of an incomplete solution, from which is taken a 4.39 ml aliquot, stored at −20° C.:

| Solutions | Volumes | Final concentrations |
|---|---|---|
| Tris-HCl 1.5M, pH 7.5 | 0.33 ml | 5 mM |
| Sucrose 1M | 25 ml | 0.25 M |

-continued

| Solutions | Volumes | Final concentrations |
|---|---|---|
| $MgSO_4$ 2 mM | 10 ml | 0.2 mM |
| EDTA 500 mM | 4 ml | 20 mM |
| Distilled water | 48.47 ml | |

The complete solution is prepared extemporaneously with:

4.39 ml of incomplete solution

+500 μl of 4% Triton X100

+10 μl of DTT (dithiothreitol), 1M

+50 μl of 0.5 mg/ml leupeptin

+50 μl of 40 mM PMSF (phenylmethanesulfonyl sulfide)

For the enzymatic activity assay, leupeptin is not added since it inhibits the activity of the proteasome.

2.1B: Protein Assay Via the Bradford Method (Refer to the Publication "a Rapid and Sensitive Method for the Quantitation of Microgram Quantities of Protein Utilizing the Principle of Protein-Dye Binding", Bradford M. Anal. Biochem. (1976) 72: 248-254)

a) Preparation of the Calibration Range:

BSA stock solution: 50 μg/ml (BIORAD; protein standard; ref. 500-0006)).

| Amount of protein (μg/tube) | BSA (μl) | $H_2O$ (μl) |
|---|---|---|
| 0 | 0 | 800 |
| 1 | 20 | 780 |
| 2 | 40 | 760 |
| 3 | 60 | 740 |
| 4 | 80 | 720 |
| 5 | 100 | 700 |
| 6 | 120 | 680 |
| 8 | 160 | 640 |

In each tube: addition of 200 μl of Coomassie blue G250.

The Coomassie blue is prepared extemporaneously by five-fold dilution of the stock solution.

b) Preparation of the Samples:

The process is performed as follows:

recovery of the cells in the lysis buffer and then ultrasonication treatment followed by assay of the protein concentration If the protein concentration>3 mg/ml, perform a 10-fold dilution and then take 100 μl of diluted cell extract +700 μl of MilliQ water +200 μl of blue or, if the concentration is low, 10 μl of cell extract +790 μl of MilliQ water +200 μl of blue Stir by vortex, wait for 5 minutes and then take the reading at 595 nm 2.1C: Proteasome Activity Assay The cells are rinsed twice with PBS and each peptidase activity of the proteasome is then determined by using a fluorogenic peptide substrate specific for each of the activities, in the presence and in the absence of a specific proteasome inhibitor, MG 132 (Leu-Leu-Leucinal). The peptide substrate products are the following: Leu-Leu-Val-Tyr-amc (LLVY-amc) for the chymotrypsin-like activity, Leu-Leu-Glu-na (LLE-na) for the post-glutamic hydrolase activity and Leu-Ser-Thr-Arg-amc (LSTR-amc) for the trypsin-like activity. The principle of the assay consists in monitoring over time the increase in fluorescence due to the release of the fluorophores aminomethylcoumarin or β-naphthylamine from the fluorogenic peptides.

a) LLVY activity (chymotrypsin-like)

a.1—Principle

Proteasome (LLVY activity (chymotrypsin-like))

N-Succinyl-LLVY-MCA→N-Succinyl-LLVY+MCA
fluorescent

Reading with a spectrofluorimeter at an excitation wavelength of 350 nm and an emission wavelength of 440 nm.

a.2—Reagents

TRIS 25 mM buffer pH 7.5

7-amino-4-methylcoumarin (MCA) (Sigma: A9891)

20 mM stock solution (3.5 mg/l ml DMSO)

Fluorogenic substrate: N-Succinyl-Leu-Leu-Val-Tyr-7-amido-4-methyl coumarin (Sigma: 56510)

10 mM stock solution in DMSO a.3—MCA (7-amino-4-methylcoumarin) Calibration Range The process is performed as follows:

Dilute the MCA stock solution to 4 μM in the TRIS buffer.

In a 96-well plate, distribute each amount in duplicate:

| Amount of MCA (μM) | MCA (μl) | TRIS (μl) |
|---|---|---|
| 0 | 0 | 200 |
| 0.1 | 5 | 195 |
| 0.2 | 10 | 190 |
| 0.3 | 15 | 185 |
| 0.4 | 20 | 180 |
| 0.5 | 25 | 175 |
| 0.6 | 30 | 170 |
| 0.7 | 35 | 165 |
| 0.8 | 40 | 160 |
| 1.0 | 50 | 150 |

Prepare a blank: 200 μl of TRIS buffer.

Read on a spectrofluorimeter at an excitation wavelength of 350 nm and an emission wavelength of 440 nm. With FLUOstar (BMG) at 355 nm and 460 nm at a gain of 40.

a.4—Assay of the LLVY Activity (Chymotrypsin-Like)

The process is performed as follows:

Into a 96-well plate, introduce in duplicate a fixed volume of cell lyzate (determined from the lowest protein concentration of the samples, which should correspond to 20 μg of protein) and make up to 100 μl with TRIS buffer.

Add 100 μl of LLVY-MCA substrate prediluted to 25 μM in the TRIS buffer (12.5 μM final).

take the spectrofluorimeter readings at an excitation wavelength of 355 nm and an emission wavelength of 460 nm with a gain of 40, every 2 minutes for 30 minutes.

a.5—Results

The raw results are expressed in F.U./minute, F.U. denoting the values supplied by the machine, expressed in fluorescence units.

The assay is performed on 200 μl of reaction volume containing a volume V of cell lyzate set as a function of the protein concentrations of the lyzates.

The proteins assayed extemporaneously are expressed in μg/μl.

From the calibration range, the activity may be expressed as follows, in pmol of MCA released/minute/mg of protein:

$$\frac{\text{Average rate } F.U./\text{min} \times 200 \times 10^{-6} \times 10^{-6} \times 10^{12}}{\text{Protein } \mu\text{g}/\mu\text{l} \times V.10^{-6} \times \text{coefficient of the slope } a}$$

with a=$4.568\times10^4$ b)—LLE Activity (Post-Glutamic Hydrolase)

b.1—Principle

The following cleavage reaction is studied:

Proteasome (LLE activity (post-glutamic hydrolase)

N-CBZ-LLE-NA→N-CBZ-LLE-+NA fluorescent

Reading on a spectrofluorimeter at an excitation wavelength of 333 nm and an emission wavelength of 410 nm.

b.2—Reagents mM TRIS buffer pH 7.5

β-Naphthylamide (NA) (Sigma: N8381)

20 mM stock solution (5.73 mg/2 ml DMSO)

Fluorogenic substrate N-CBZ-Leu-Leu-Glu-β-Naphthylamine (Sigma: C0788)

10 mM stock solution in DMSO b.3—NA ((β-Naphthylamide) Calibration Range

The calibration is performed as follows:

Dilute the NA stock solution to 4 μM in the TRIS buffer.

In a 96-well plate, distribute each amount in duplicate:

As indicated in the table below.

| Amount of NA. (μM) | NA (μl) | TRIS (μl) |
|---|---|---|
| 0 | 0 | 200 |
| 0.1 | 5 | 195 |
| 0.2 | 10 | 190 |
| 0.3 | 15 | 185 |
| 0.4 | 20 | 180 |
| 0.5 | 25 | 175 |
| 0.6 | 30 | 170 |
| 0.7 | 35 | 165 |
| 0.8 | 40 | 160 |
| 1.0 | 50 | 150 |

Prepare a blank: 200 μl of TRIS buffer.

Read on a spectrofluorimeter at an excitation wavelength of 333 nm and an emission wavelength of 410 nm. With FLUOstar (BMG) at 340 nm and 410 nm with a gain of 83.

b.4—Assay of the LLE Activity (Post-Glutamic Hydrolase)

The process is performed as follows:

In a 96-well plate, introduce in duplicate a fixed volume of cell lyzate (determined from the lowest protein concentration of the samples, which should correspond to 20 μg of protein) and make up to 100 μl with TRIS buffer.

Add 100 μl of LLE-NA substrate prediluted to 300 μM in the TRIS buffer (150 μM final).

Take the spectrofluorimeter readings at an excitation wavelength of 340 nm and an emission wavelength of 410 nm at a gain of 83 every 2 minutes, for 35 minutes.

b.5—Results

The raw results are expressed in F.U./min.

The assay is performed on 200 μl of reaction volume containing a volume V of cell lyzate set as a function of the protein concentrations of the lyzates.

The proteins assayed extemporaneously are expressed in μg/μl.

From the calibration range, the activity may be expressed in pmol of MCA released/minute/mg of protein:

$$\frac{\text{Average rate } F.U./\text{min} \times 200 \times 10^{-6} \times 10^{-6} \times 10^{12}}{\text{Protein } \mu\text{g}/\mu\text{l} \times V.10^{-3} \times \text{coefficient of the slope } a}$$

with a=$0.966\times10^4$ c) LSTR Activity (Trypsin-Like)

c.1—Principle

Proteasome (LSTR Activity (Trypsin-Like))

Nt Boc LSTR-MCA→Nt Boc LSTR+MCA fluorescent

Reading on a spectrofluorimeter at an excitation wavelength of 350 nm and an emission wavelength of 440 nm.

c.2—Reagents 25 mM TRIS buffer pH 7.5

7-amino-4-methylcoumarin (MCA) (Sigma: A9891)

20 mM stock solution (3.5 mg/1 ml DMSO)

Fluorogenic substrate: N-t-BOC-Leu-Ser-Thr-Arg7-7-amido-4-methyl coumarin (Sigma: B4636)

10 mM stock solution in DMSO

Proteasome inhibitor: Mg132 (Z-Leu-Leu-Leu-CHO) (Affinity, ZW8440)

20 mM stock solution in DMSO c.3—MCA Calibration Range

The calibration curve is plotted as follows: (see table below)

Dilute the MCA stock solution to 4 μM in the TRIS buffer

In a 96-well plate, distribute each amount in duplicate

| Amount of MCA (μM) | MCA (μl) | TRIS (μl) |
|---|---|---|
| 0 | 0 | 200 |
| 0.1 | 5 | 195 |
| 0.2 | 10 | 190 |
| 0.3 | 15 | 185 |
| 0.4 | 20 | 180 |
| 0.5 | 25 | 175 |
| 0.6 | 30 | 170 |
| 0.7 | 35 | 165 |
| 0.8 | 40 | 160 |
| 1.0 | 50 | 150 |

Prepare a blank: 200 μl of TRIS buffer.

Read on a spectrofluorimeter at an excitation wavelength of 350 nm and an emission wavelength of 440 nm. With FLUOstar (BMG) at 355 nm and 460 nm at a gain of 30.

c.4—Assay of the LSTR Activity

In a 96-well plate, introduce in duplicate a fixed volume of cell lyzate (determined from the lowest protein concentration of the samples, which should correspond to 50 μg of protein) and make up to 100 μl with TRIS buffer.

Add 100 μl of LSTR-MCA substrate prediluted to 80 μM in the TRIS buffer (40 μM final).

In parallel, check that it is indeed the proteasome activity by testing the inhibitor Mg132.

Add to 50 μg of protein 10 μl of solution of Mg132 prediluted to 400 μM in the TRIS buffer (20 μM final) and make up to 100 μl with TRIS buffer. Next, add 100 μl of LSTR substrate prediluted to 80 μM in the TRIS buffer (40 μM final).

Take the spectrofluorimeter readings at an excitation wavelength of 355 nm and an emission wavelength of 460 nm at a gain of 30, every 2 minutes, for 30 minutes.

c.5—Results

The raw results are expressed in F.U./min.

The assay is performed on 200 μl of reaction volume containing a volume V of cell lyzate set as a function of the protein concentrations of the lyzates.

The proteins assayed extemporaneously are expressed in μg/μl.

From the calibration range, the activity may be expressed in pmol of MCA released/minute/mg of protein:

$$\frac{\text{Average rate } U.F./\text{min} \times 200 \times 10^{-6} \times 10^{-6} \times 10^{12}}{\text{Protein } \mu\text{g}/\mu\text{l} \times V.10^{-3} \times \text{coefficient of the slope } a}$$

with $a=1.728\times10^4$ 2.1D: Measurement of the tyrosinase activity

Principle of the Assay:

The assay is based on measuring the dopa-oxidase activity of tyrosinase. The principle of the assay is based on the detection of dopachrome, which absorbs at 475 nm on FLU-Ostar (BMG)

Materials:

Lysis buffer

Substrate: L-DOPA (Sigma, D-9628, MW 197.2) at 10 mM in PBS, prepared extemporaneously due to the autoxidation of L-Dopa.

Human melanocytes in culture were treated with 25 μM of linoleic acid (±120 nM Mg132) or 25 μM of palmitic acid (±120 nM Mg132) or 5 μg/ml of *Phaeodactylum* (±120 nM Mg132) in MNT1 medium containing 1% BSA, 50 μM vitamin E and 1 mM vitamin C. The melanocytes were recovered and lyzed 72 hours after treatment. 50 μg of extract are then incubated with 1 mM of L-Dopamine for one hour at 37° C. Measurement of the tyrosinase activity is performed at 475 nm every 2 minutes using a microplate reader thermostatically maintained at 37° C.

The Dopa-oxidase activity is obtained as OD/min/mg of protein. The blank is prepared with lysis buffer in the presence of L-DOPA.

2.2 Treatment of MNT1 in Order to Assay the Proteasome, the Ubiquitin Proteins and the Tyrosinase by Western Blotting 2.2A: Cell Culture a) Protocol:

Inoculation on D0

$10^6$ MNT1 cells/dish 35 mm in diameter, in quadruplicate in MNT1 medium, 2 ml/dish Treatment on D1

Linoleic acid 25 μM

Palmitic acid 25 μM

*Phaeodactylum* 5 μg/ml in MNT1 medium

+1% bovine serum albumin (BSA)+Vitamin E (Vitamin E) 50 μM+Vitamin C (Vitamin C) 1 mM Linoleic acid 25 μM Palmitic acid 25 μM

*Phaeodactylum* 5 μg/ml in MNT1 medium

+1% BSA+Vitamin E 50 μM+Vitamin C 1 mM

+120 nM Mg132

Stirring with a magnetic bar at 37° C. for 1 hour

Preparation of the Lyzates on D2, D3 and D4

2 rinses with PBS

Recovery of the cell lawn in 150 μl of Laemmli 2× buffer+1% DTT (10 mM) by scraping.

2 dishes/Eppendorf tube

Freezing at ±20° C.

Protein Assay (Bradford) and Western Blotting

The protein assay method is the same as that used previously, as is the Western blotting method.

After assaying the proteins in Eppendorf tubes, the samples are diluted in Laemmli 2× buffer in order to obtain 1 μg/μl of protein. To these sample solutions are added 10× bromophenol blue. The samples can be frozen at −20° C.

b) Media and Reagents

MNT-1 Culture Medium

DMEM 4.5 g/ml of glucose (Gibco: 61965-026)

+20% FCS

+10% supplement AIMV (Gibco: 12055-091)

+1% Sodium pyruvate 100 mM (Gibco: 12360-039)

+1% NEAA (Gibco: 11140-035)

Stock Solutions

Linoleic acid (Sigma; L1012)

2.8 mg/ml in EtOH (0.25% in medium)

Palmitic acid (Sigma; P5585)

2.56 mg/ml in EtOH (0.25% in medium)

*Phaeodactylum*

2 mg/ml in EtOH (0.25% in medium)

Vitamin C 25.6 mg/ml in PBS (1% in medium)

Vitamin E 21.55 mg/ml in EtOH (0.1% in medium)

Mg132 (Sigma; C2211)

120 μM in DMSO (0.1% in medium)

Lysis Buffer

1M DL-dithiothreitol solution (Sigma; ref. D0632 stored at 4° C.)

0.154 g to be dissolved in 1 ml of distilled water.

Take a 10 μl aliquot and store at −20° C.

Laemmli 2× sample reducing agent buffer (denaturating agent)

Tris-HCl 0.06M pH6.8; SDS 2.3%; Glycerol 10%

| | |
|---|---|
| concentration gel buffer Tris 0.5M pH 6.8 | 6.25 ml |
| SDS 10% | 11.50 ml |
| Glycerol | 5 ml |
| Distilled water to make up to 50 ml | |

2.2B: Western-blot a) Preparation of the Samples et Electrophoresis

Electrophoresis of the proteins is performed in a polyacrylamide minigel 1 mm to 1.5 nm thick, under denaturing and reducing conditions, in batch buffer according to the Laemmli method (1970). The gels containing 12% T, 2.7% C allow separation of the low molecular weight proteins ranging from 20 to 120 kDa. The gels containing 8% T; 2.7% C allow separation of the high molecular weight proteins from 35 to 250 kDa.

All the solutions required for producing the gels are presented in Appendix A hereinbelow.

Separation Gel

This gel may be poured either the day before or on the day itself, but in any case one to two hours before migration.

Pouring of the gel is performed using a pipette up to about 0.5 mm from the bottom of the comb provided for the concentration gel. Absolute ethanol is added gently to the surface to obtain a uniform baseline (±1 ml/gel).

Concentration Gel (Stacking Gel)

The ethanol is removed.

2.5 ml of gel are poured using a polyethylene Pasteur transfer pipette (Biorad, ref. 223-9528) and the combs are then inserted. After one hour, the gel is polymerized.

Preparation of the Samples

Before recovering the cells from the dishes, they are rinsed twice with PBS. After the final rinsing, the maximum amount of PBS is removed. The cells are recovered in the Laemmli 2× buffer+10 mM of DTT (see Appendix A below) by scraping ($5\times10^6$ cells/ml of lysis buffer minimum). The lyzates recovered in 1.5 ml Eppendorf tubes are frozen at −20° C.

Before performing the electrophoresis, the thawed lyzates are heated at 95° C. for 10 minutes and the proteins are assayed.

The protein assay is performed during the polymerization of the separation gel or the day before (see Appendix C).

In Eppendorf tubes, the samples are diluted in Laemmli 2× buffer in order to obtain identical solutions≦1 μg/μl of protein. To these sample solutions are added 10× bromophenol blue.

Application

The samples are heated at 95° C. for 5 minutes.

The volume to be applied depends on the desired amount of protein (maximum volume=25 μL for a 1 mm gel and 40 μL for a 1.5 mm gel). 10 μg of protein, i.e. 10 μl, is the reference amount, and it is then adapted according to the expression of the target protein.

The combs are removed. 200 ml of 1× migration buffer are poured onto the gels, in the central compartment between the two gels, taking care to ensure leaktightness, and then into the quartz cell.

The samples are applied using an adapted tapered tip on the micropipette, and also 10 μl of prestained molecular mass controls (Biorad, Prestained SDS-PAGE standards Low Range; ref. 161-0305) or (Amersham, Full Range Rainbow; ref. RPN800W).

Migration

The electrophoresis is performed at room temperature, at 200 V. It is stopped when the migration front has left the gel (about 40 minutes of migration).

b) Semi-Dry Transfer of the Proteins onto Membrane

Two thick sheets of filter paper (Biorad, ref 17033960) and the cellulose membranes (Biorad, ref. 162-0115) are soaked in the Towbin et al. (1979) transfer buffer that is the origin of this method (see Appendix B).

In the semi-dry transfer apparatus (Biorad), a moistened thick sheet of filter paper is placed on the anode.

Once the migration is complete, the concentration gel is removed and the separation gel is applied to the cellulose membrane. The membrane and the gel are placed on the sheet of filter paper. The second sheet of filter paper is applied to gel.

During the manufacture of the "sandwich", all air bubbles must be removed using a glass stem, since they would give rise to transfer. The apparatus is closed with a lid that forms the cathode.

The protein transfer is performed at 10 V for 1 hour 30 minutes.

c) Marking with Ponceau Red

To check the quality of the transfer, the proteins are stained with Ponceau red (Sigma; P7170).

The cellulose membrane is rinsed with MilliQ water and then soaked in a bath of 1× Ponceau red for 10 minutes with stirring. It is then washed in several baths of MilliQ water until the stain remains only on the protein bands.

The membrane is inserted into a plastic and scanned.

The protein bands may be quantified to determine the total amount of transferred proteins.

d) Blocking of the Aspecific Binding Sites

The membrane is stirred overnight at 4° C. or for 1 hour 30 minutes at room temperature in a solution for blocking the aspecific binding sites formed from 5% skimmed milk (Régilait) in PBS-T buffer prepared in Appendix B hereinbelow (20 ml/membrane).

e) Immunodetection

The references and the optimum dilutions of the antibodies are in Appendix D hereinbelow.

After blocking the non-specific sites, the membrane is rinsed rapidly in PBS-T.

Next, this membrane is placed in contact with the primary antibody diluted to the optimum concentration in PBS-T with or without 5% milk (m/v) depending on the antibody, for 1 hour with stirring at room temperature or overnight at 4° C.

It is then rinsed rapidly for three times 10 minutes in PBS-T in order to remove the excess unbound free antibody.

Next, it is placed in contact with the adequate peroxidase-coupled secondary antibody diluted in PBS-T or 5% milk (5 ml) with stirring at room temperature.

After incubation for 45 minutes, it is rinsed rapidly twice, and then washed five times for 5 minutes with PBS-T buffer and a final time in 1×PBS.

After draining, it is placed on a kitchen film (SARAN), "protein"-side up.

The membrane is revealed using a highly sensitive chemiluminescence detection kit (Amersham; ECL Western blotting ref RPN2209), using luminol as peroxidase substrate. Under the action of peroxidase and an amplifier, the luminol is oxidized and goes into a transient excited state. Return to the ground state takes place by emission of photons, which strike an autoradiography film placed on the membrane.

1 ml of each of the two solutions of the detection kit are mixed (2 ml, minimum volume required for covering the membrane).

Immediately, the mixture is poured uniformly onto the membrane and left in contact for exactly one minute at room temperature.

The drained membrane is sealed under Saran kitchen film and placed in a cassette protected from light, and then covered with a preflashed autoradiography film (Amersham, Hyperfilm ECL ref. RPN2103K).

After exposure for 5 minutes, the autoradiography film is developed. A new film is re-exposed if necessary, to optimize the desired signal (up to 1 hour).

The bands are quantified by means of the Gels Analysts 3.01 software.

2.3 Preparation of MNT-1 Protein Extracts in Order to Perform Tyrosinase Immunoprecipitations 2.3A: Cell Culture a) Protocol Inoculation on D0

$10^6$ MNT1 cells/dish 35 mm in diameter, in triplicate

In the MNT1 medium 2 ml/dish

Treatment on D1

Linoleic acid 25 μM

Palmitic acid 25 μM

*Phaeodactylum* 2.5 and 5 μg/ml in MNT1 medium

+1% BSA+Vitamin E 50 μM+Vitamin C 1 mM

Linoleic acid 25 μM

Palmitic acid 25 μM

*Phaeodactylum* 2.5 and 5 μg/ml
in MNT1 medium
+1% BSA+Vitamin E 50 μM+Vitamin C 1 mM
+120 nM Mg132
Stirring with a magnetic bar at 37° C. for 1 hour
Preparation of the Lyzates and Counting on D2
2 rinses with PBS
On a bed of ice;
recovery in 150 μl of lysis buffer
by scraping.
Freezing at ±20° C.
rinsing with PBS
+0.5 ml Trypsin/EDTA
+0.5 ml PBS+10% FCS
Counting on a Z2 Counter
On 0.5 ml of suspension+10 ml Isoton
b) Media and Reagents
MNT1 Culture Medium
DMEM 4.5 g/ml of glucose (Gibco: 61965-026)
+20% FCS
+10% supplement AIMV (Gibco: 12055-091)
+1% Sodium pyruvate 100 mM (Gibco: 12360-039)
+1% NEAA (Gibco: 11140-035)
Stock Solutions
Linoleic acid (Sigma; L1012)
2.8 mg/ml in EtOH (0.25% in medium)
Palmitic acid (Sigma; P5585)
2.56 mg/ml in EtOH (0.25% in medium)
*Phaeodactylum*
2 mg/ml in EtOH (0.25% in medium)
Vitamin C
25.6 mg/ml in PBS (1% in medium)
Vit E
21.55 mg/ml in EtOH (0.1% in medium)
Mg132 (Sigma; C2211)
120 μM in DMSO (0.1% in medium)
Lysis Buffer
Tris-HCl 1.5 M, pH7.5

45.375 g of Tris base (Sigma; T1503) to be dissolved in 200 ml of distilled water, adjust the pH to 7.5 with 12N HCl and then make up to 250 ml 1M sucrose solution (Merck; ref 7654)

8.55 g to be dissolved in 20 ml of distilled water, and then adjust to 25 ml.

2 mM $MgSO_4$ solution (Sigma; ref. M7506)

6 mg to be dissolved in 25 ml of distilled water.

Or $MgSO_4.7H_2O$ (Sigma; ref. M5921) 12.4 mg to be dissolved in 25 ml of distilled water;

store at 4° C.

4% Triton X100 solution (Sigma; ref. X100)

0.8 g to be dissolved in 20 ml of distilled water (very slow)

Take a 0.5 ml aliquot and store at −20° C.

40 mM PMSF solution (Sigma; ref. P7626)

14 mg to be dissolved in 2 ml of absolute ethanol.

Take a 50 μl aliquot and store at 4° C., for 9 months 0.5 mg/ml leupeptin solution (Sigma; ref. L2884; stored at −20° C.)

Water-soluble. Take a 50 μl aliquot and store at −20° C., for 1 month.

1M DL-dithiothreitol solution (Sigma; ref. D0632 stored at 4° C.)

0.154 g to be dissolved in 1 ml of distilled water.

Take a 10 μl aliquot and store at −20° C.

500 mM tetrasodium EDTA solution (Sigma; ref. ED4S)

3.8 g to be dissolved in 20 ml of distilled water; stored at 4° C.

Preparation of the Lysis Buffer (Per 100 mL)

Preparation of an incomplete solution, from which a 4.39 ml aliquot is taken, stored at −20° C.:

| Solutions | Volumes | Final concentrations |
|---|---|---|
| Tris-HCl 1.5M, pH 7.5 | 0.33 ml | 5 mM |
| Sucrose 1M | 25 ml | 0.25 M |
| $MgSO_4$ 2 mM | 10 ml | 0.2 mM |
| EDTA 500 mM | 4 ml | 20 mM |
| Distilled water | 48.47 ml | |

The complete solution is prepared extemporaneously with:
4.39 ml of incomplete solution
+500 μl of 4% Triton X100
+10 μl of 1M DTT
+50 μl of 0.5 mg/ml leupeptin
+50 μl of PMSF at 40 mM For the enzymatic activity assay, leupeptin is not added since it inhibits the activity of the proteasome.

2.3B: Immunoprecipitation Protocol

Human melanocytes in culture were treated with 25 μM of linoleic acid (±120 nM Mg132) or 25 μM of palmitic acid (±120 nM Mg132) or 5 μg/ml of *Phaeodactylum* (±120 nM Mg132) in an MNT1 medium containing 1% BSA, 50 μM vitamin E and 1 mM vitamin C. The melanocytes are recovered and lyzed at 24 or 72 hours after treatment.

The lyzate (500 μg of protein) was incubated with 10 μL of anti-tyrosinase antibody (Tyrosinase Ab-1 monoclonal antibody (clone T311) Lab vision corporation) or anti-ubiquitin monoclonal antibody (Anti-monoubiquitin monoclonal (SC-8017, Santa Cruz)) for 1 hour at 4° C. This mixture was then treated with 50 μl of A-Sepharose protein (Amersham Pharmacia Biotech, 17-5280-01) and incubated for 16 hours at 4° C. The mixture is then centrifuged at 1000×g for 5 minutes. The pellet is washed and resuspended with 200 μL of PBS, 1% NP40 ((Amersham Pharmacia Biotech, US19628) and centrifuged at 1000×g for 5 minutes. After three successive washes, the pellet was placed on SDS-PAGE gels and then transferred onto a nitrocellulose membrane. The membrane was then incubated with an anti-tyrosinase monoclonal antibody for one hour (Tyrosinase Ab-1 monoclonal antibody (clone T311) Lab vision corporation) (1/2000). The western blot was developed by means of a peroxidase-coupled anti-mouse immunoglobulin antibody (1/5000), and the ECL kit (Amersham Pharmacia Biotech, NA9310).

3. Results 3.1 Modulation of the Proteasome Activity Induced by Adding Extracts of the Alga *Phaeodactylum Tricornutum* to the MNT-1 Melanocyte Line In order to characterize the influence of the extracts of the alga *Phaeodactylum tricornutum* on melanin synthesis, various cultures of melanocyte cells of the MNT-1 line were prepared (culture medium supplemented or otherwise with extracts of the alga *Phaeodactylum tricornutum*, with fatty acids, or with a proteasome-dependent proteolysis inhibitor Mg132).

As outlined previously, a previous study revealed that the melanocyte culture in the presence of linoleic acid led to a decrease in the amount of melanin, by promoting the degradation of tyrosinase by the proteasome; and that the same culture prepared in the presence of palmitic acid brought about an inverse effect. These two compounds (linoleic acid and palmitic acid) were used, respectively, as positive and negative control to characterize the effect of the extracts of the alga *Phaeodactylum tricornutum* on the activity of tyrosinase, a limiting enzyme of melanin synthesis that governs skin pigmentation. From these same cell extracts of the MNT-1 melanocyte line, a study of the proteasome activity was performed. Using fluorogenic synthetic substrate peptides, specific for the three catalytic sites of proteasome 20S, the proteasome activities were measured.

In parallel, using specific antibodies, the 20S and 26S forms of the proteasome were quantified by western blotting.

For the assay of the proteasome activities, the cells were lyzed at 72 hours after the cell treatment, and the protein concentration was determined.

Figure 1B:
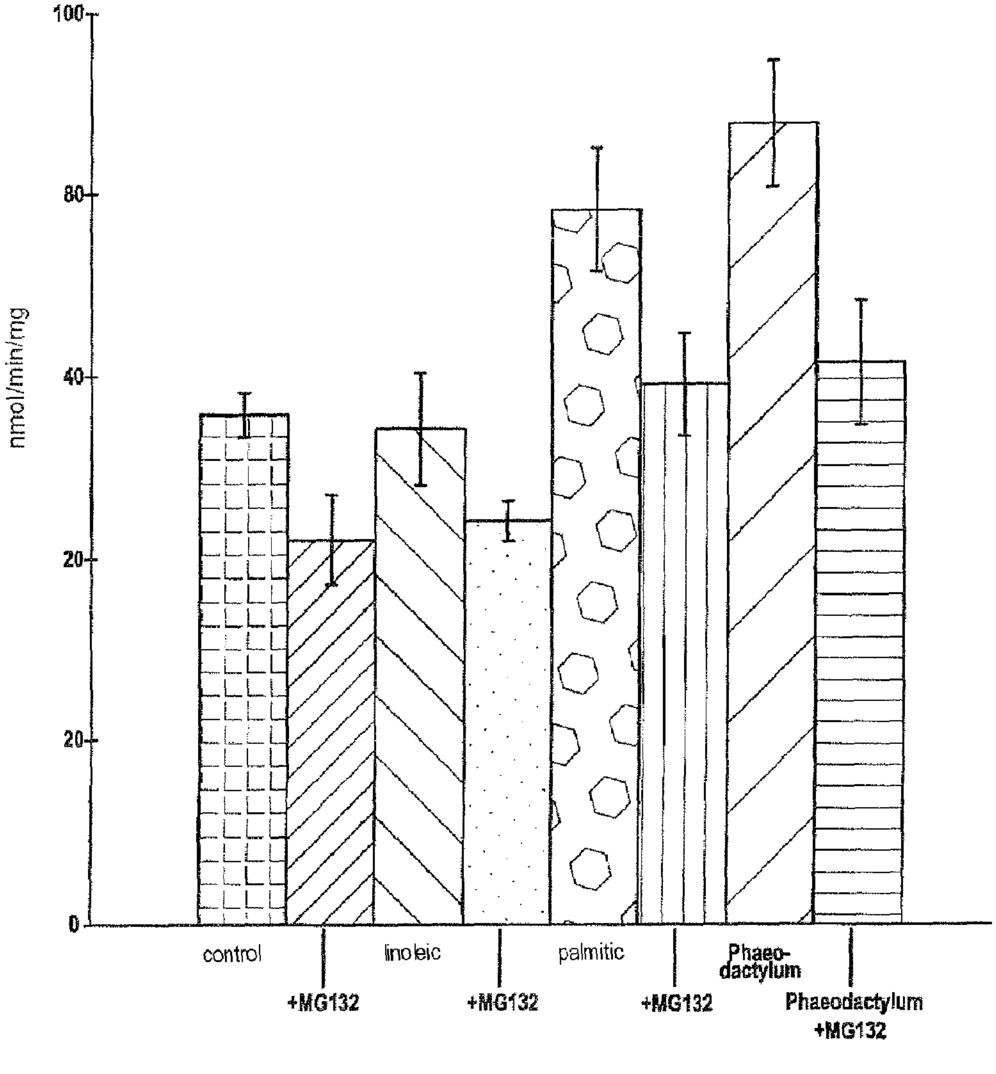
FIG. 1B: the post-glutamic-like hydrolase activity.
Figure 1C:
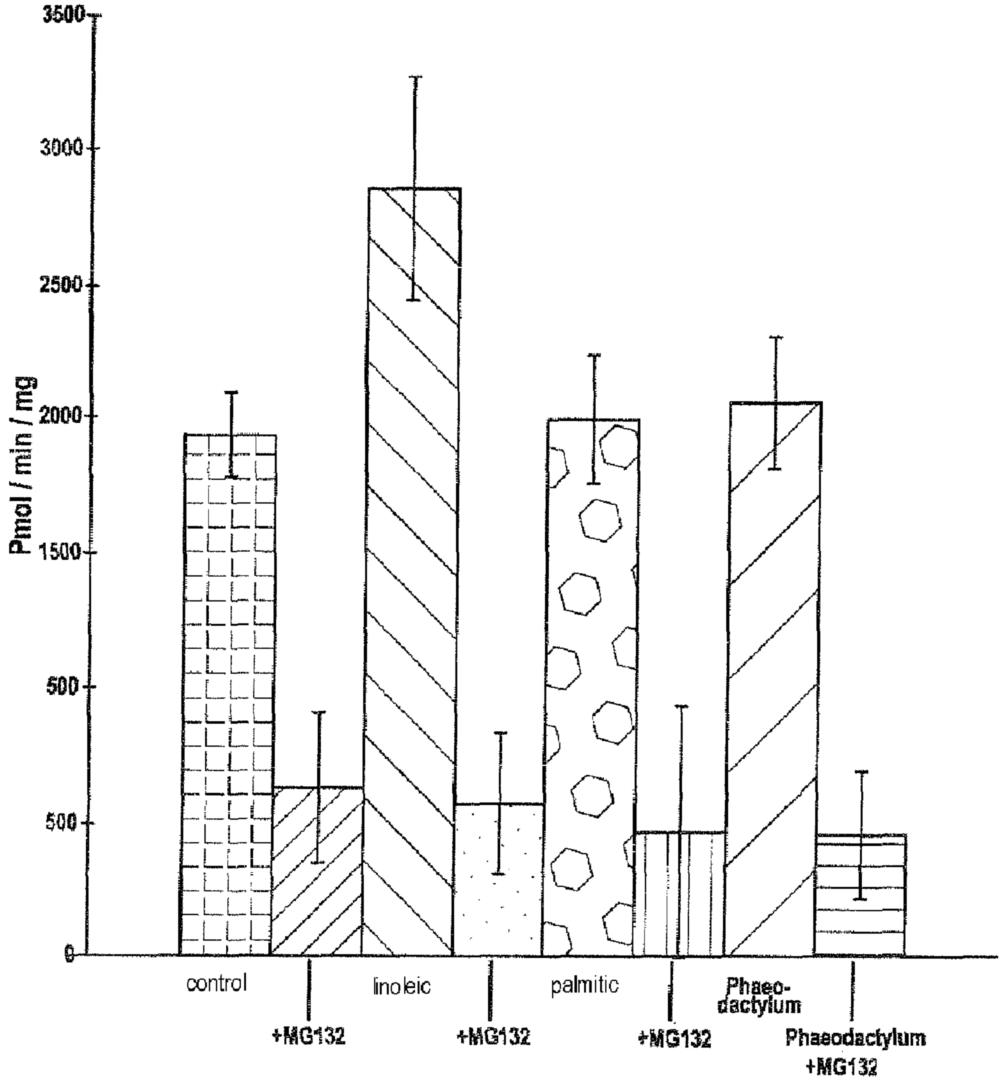
FIG. 1C: the trypsin-like activity.

The results given in FIGS. 1A, 1B and 1C show that 72 hours after addition of the algal extract (Ph) or of linoleic acid, the three peptidase activities of the proteasome, measured using fluorogenic peptides, increase and do so significantly (chymotrypsin-like, post-glutamic hydrolase and trypsin-like activities).

Moreover, in the melanocytes treated with palmitic acid for 72 hours, the two peptidase activities are reduced (chymotrypsin-like and post-glutamic hydrolase activities). The proteasome activities measured using cell extracts of the MNT-1 line cultured in the presence of a proteasome-dependent proteolysis inhibitor Mg132, serve as a positive control. All these results are collated in Table 1 in the appendix.

For the purpose of determining the cause of this activation of the peptidase activities of the proteasome, we evaluated via the western blotting technique the amount of proteasome in the homogenates obtained from the lysis of MNT-1 24 hours and 72 hours after their treatment with extracts of the alga *Phaeodactylum tricornutum*, with fatty acids, or with a proteasome-dependent proteolysis inhibitor Mg132).

Figure 2A:
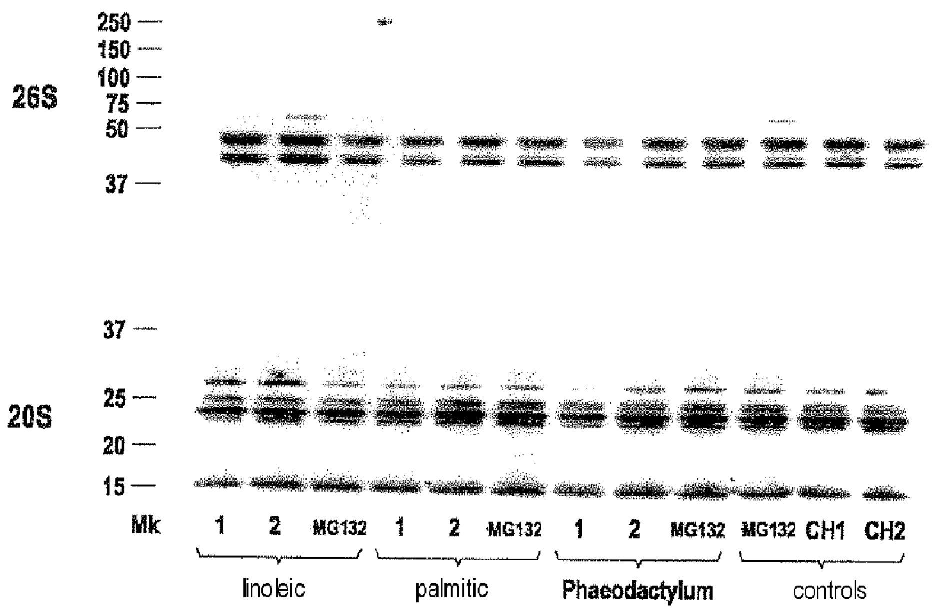
FIG. 2A: the results of the anti-proteasome western blot, obtained for lyzes at 24 hours.
Figure 2B:
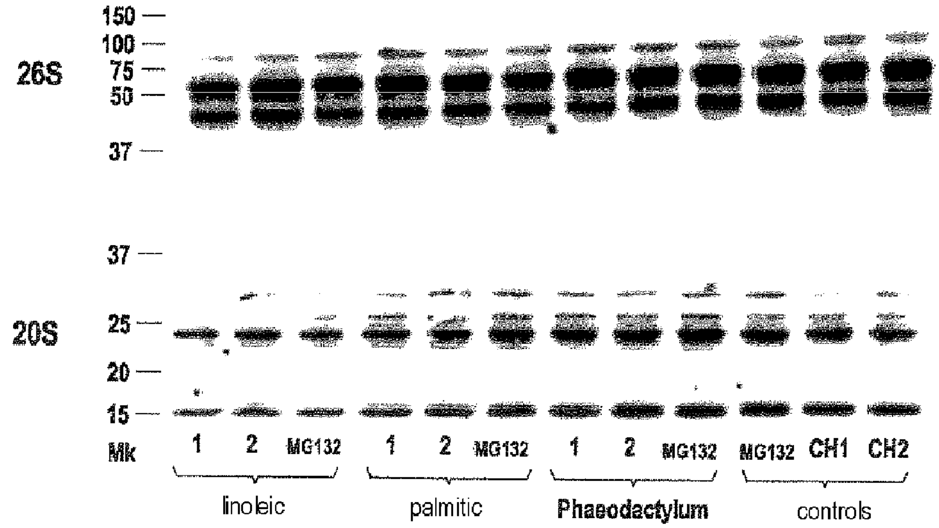
FIG. 2B: the results of the anti-proteasome western blot, obtained for lyzes at 72 hours.

The results given in FIGS. 2A and 2B show that these treatments do not modify the amount of proteasome in the cell extracts.

These results indicate that stimulation of the proteasome activity with the extracts of the alga *Phaeodactylum tricornutum* or with linoleic acid does not modify the expression or distribution of the 20S and 26S forms of the proteasome, in cells of the MNT-1 melanocyte line.

Figure 3A:
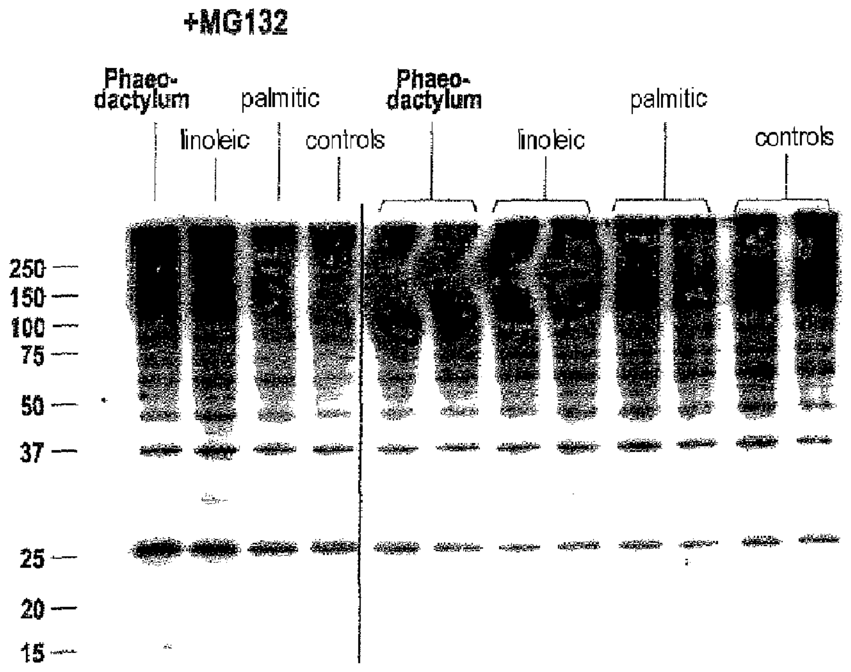
FIG. 3A: the results of the anti-ubiquitin western blot, obtained for lyzes at 24 hours.
Figure 3B:
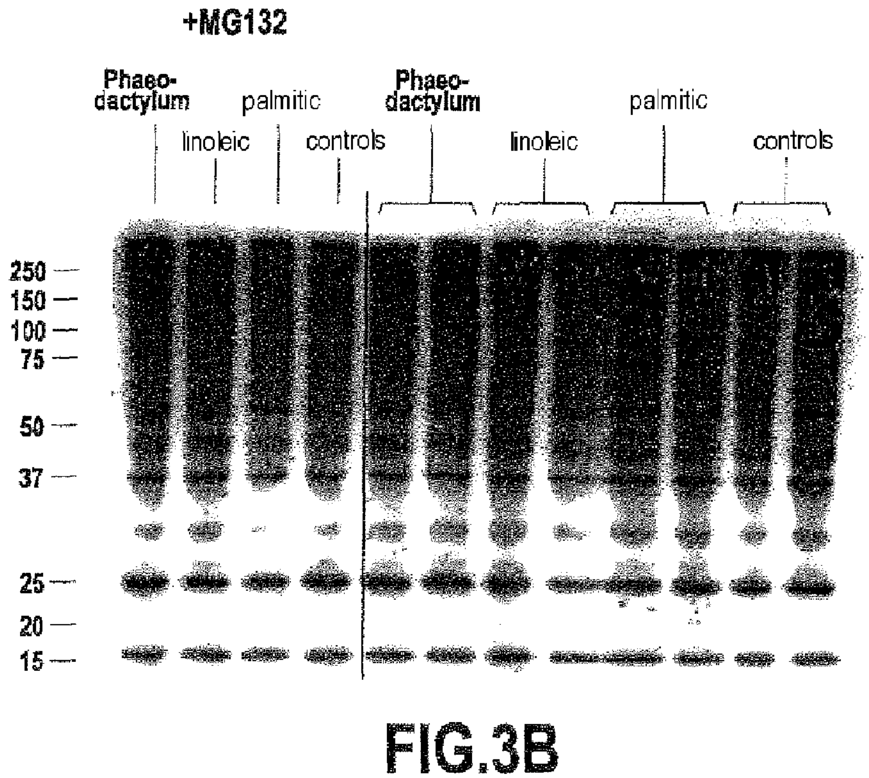
FIG. 3B: the results of the anti-ubiquitin western blot, obtained for lyzes at 72 hours.

3.2 Status of the Ubiquitin-Modified Proteins Following Addition of Extracts of the Alga *Phaeodactylum Tricornutum* to the MNT-1 Melanocyte Line We have shown that, 24 hours or 72 hours after treatment with the fatty acids or the algal extract, the level of ubiquitin proteins (FIG. 3A, 3B) was not modified except when the cells were cultured in the presence of a proteasome inhibitor, Mg132.

These observations demonstrate that the ubiquitination machinery is not affected by the treatments with the alga or with linoleic acid.

3.3 Modulation of the Tyrosinase Expression and Activity, Induced by Adding Extracts of the Alga *Phaeodactylum Tricornutum* to the MNT-1 Melanocyte Line Starting with cell extracts of MNT-1 melanocytes cultured under these various conditions, with the protocols defined in the "Materials and methods" section, the effects of the extracts of the alga *Phaeodactylum tricornutum* on the amount of tyrosinase and of its activity were characterized.

Figure 4A:
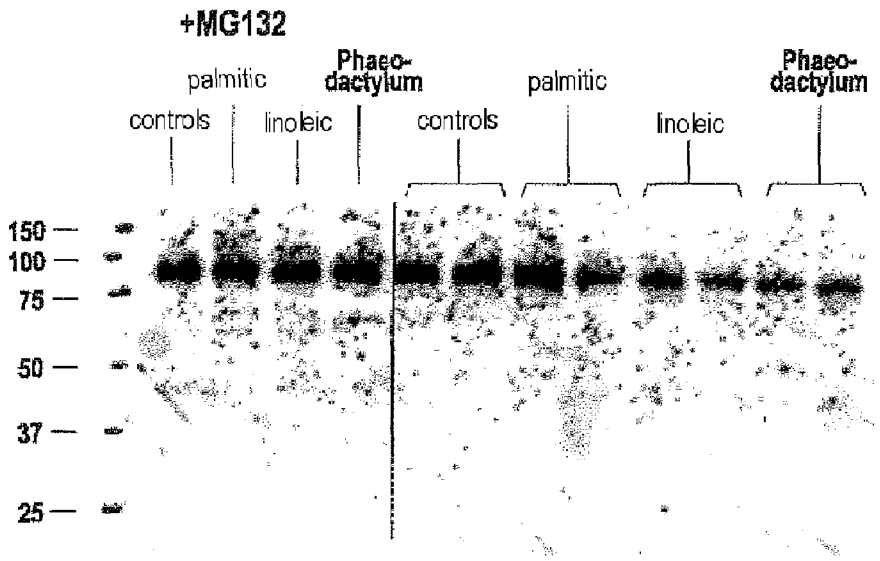
FIG. 4A: the results of the anti-tyrosinase western blot, for lyzes at 24 hours.
Figure 4B:
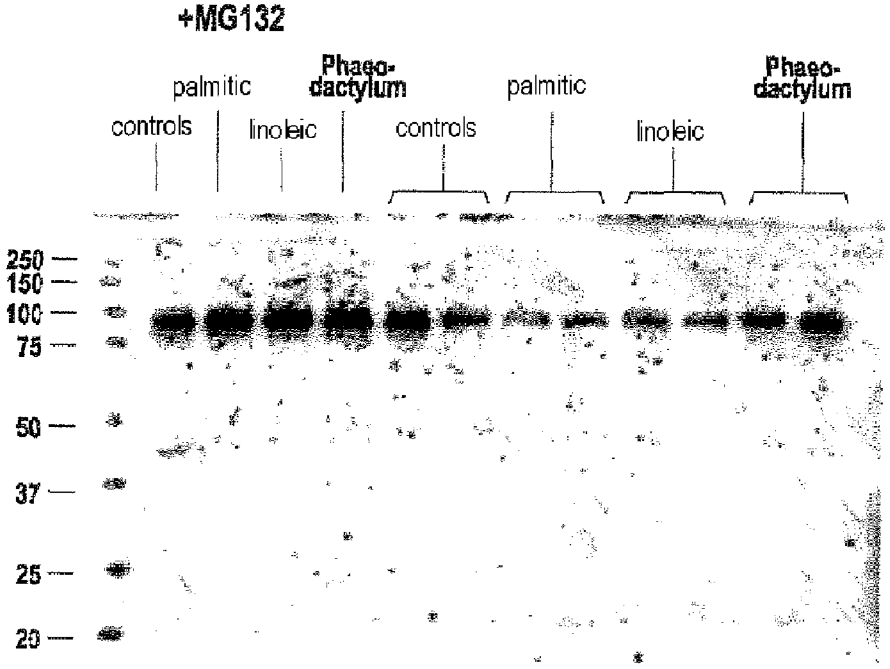
FIG. 4B: the results of the anti-tyrosinase western blot, for lyzes at 72 hours.

We have shown that, 24 hours or 72 hours after treatment of MNT-1 melanocytes with *Phaeodactylum tricornutum* or with linoleic acid, a significant decrease in tyrosinase is observed (FIGS. 4A and 4B), and that this decrease may be reversed when the cells are treated with Mg132, which is a proteasome inhibitor.

We quantified this decrease using the Image master 1D software (Amersham Pharmacia) and the results are given in Tables 2 and 3.

These preliminary observations demonstrate that tyrosinase is a physiological substrate of proteasome, and that its degradation may be activated with extracts of the alga *Phaeodactylum tricornutum.*

Figure 5:
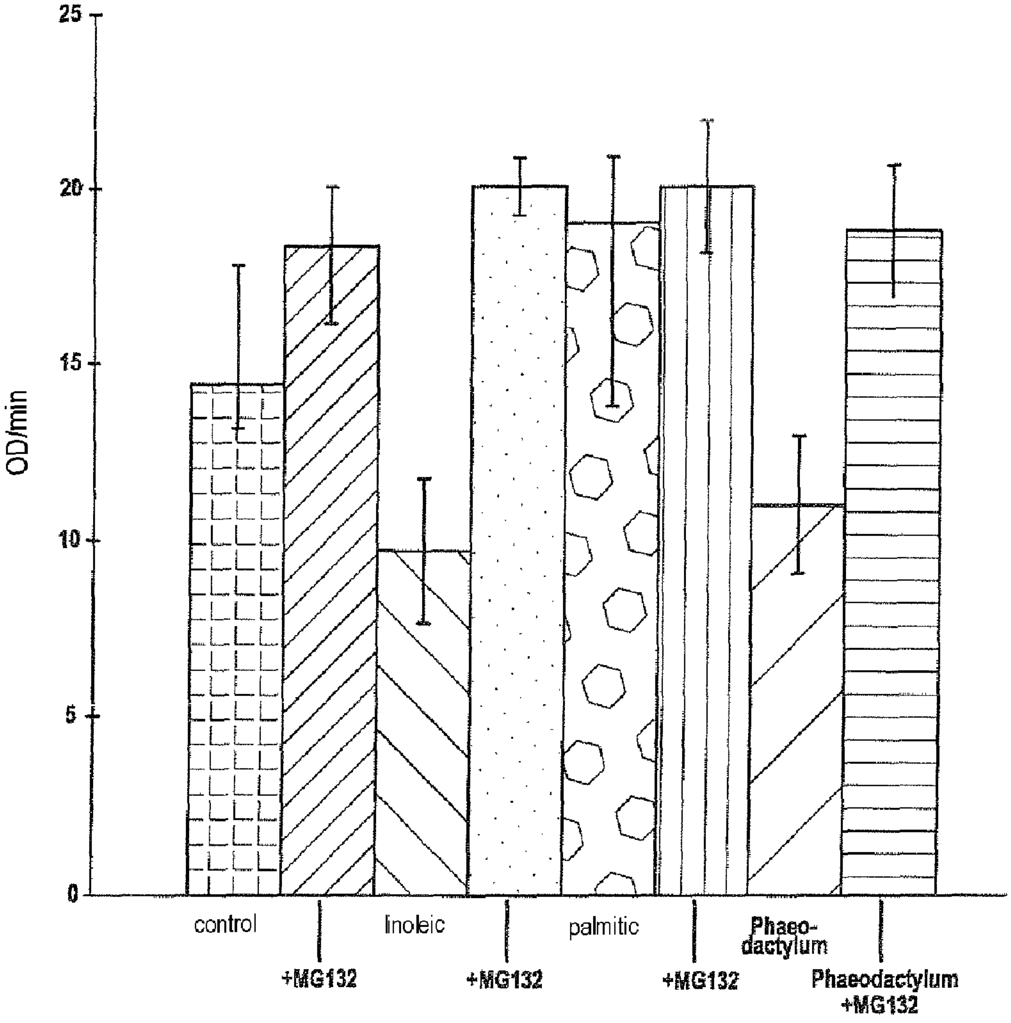
FIG. 5: measurement of the tyrosinase activity.

In a first stage, the development of a specific technique for assay of the tyrosinase activity, applicable to the cell extracts of the MNT-1 line, was undertaken. We measured the tyrosinase activity in the cells 72 hours after treatment of MNT-1 melanocytes with *Phaeodactylum tricornutum* or with linoleic acid, and we observed a significant decrease in this activity (FIG. 5 and Table 4).

TABLE 2

Quantification of tyrosinase at 24 hours

| Control (%) | Palmitic acid | Linoleic acid | Phaedactylum tricornutum | Control + Mg132 | Palmitic acid + Mg132 | Linoleic acid + Mg132 | Phaedactylum tricornutum + Mg132 |
|---|---|---|---|---|---|---|---|
| 100 | 135 | 75 | 60 | 100 | 98 | 110 | 111 |
| 100 | 127 | 51 | 56 | | | | |

TABLE 3

Quantification of tyrosinase at 72 hours

| Control (%) | Palmitic acid | Linoleic acid | Phaedactylum tricornutum | Control + Mg132 | Palmitic acid + Mg132 | Linoleic acid + Mg132 | Phaedactylum tricornutum + Mg132 |
|---|---|---|---|---|---|---|---|
| 100 | 62 | 13 | 26 | 100 | 132 | 107 | 115 |
| 100 | 88 | 22 | 24 | | | | |

TABLE 4

Tyrosinase activity at 72 hours

| Control (OD/min) | Palmitic acid | Linoleic acid | Phaedactylum tricornutum | Control + Mg132 | Palmitic acid + Mg132 | Linoleic acid + Mg132 | Phaedactylum tricornutum + Mg132 |
|---|---|---|---|---|---|---|---|
| 14.3 ± 3.5 | 18.75 ± 1.9 | 9.65 ± 2 | 11.2 ± 0.37 | 18.35 ± 1.55 | 19.8 ± 2 | 19.9 ± 0.74 | 18.7 ± 2 |

Figure 6:
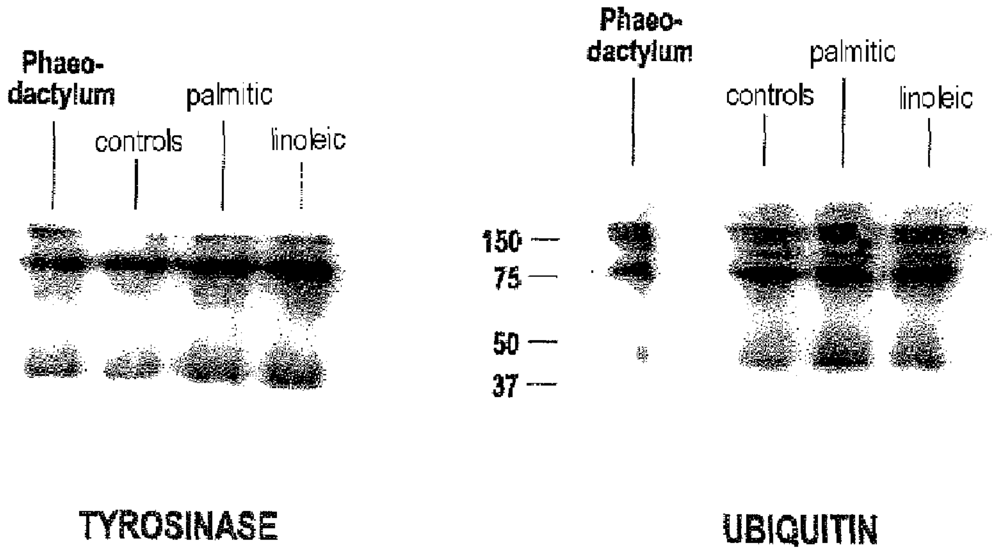
FIG. 6: the result of the immunoprecipitation tests.

To check that the proteasome substrate tyrosinase was better degraded in extracts of melanocyte cells of the MNT-1 line treated with extracts of the alga *Phaeodactylum tricornutum*, a qualitative and quantitative study of tyrosinase and of the ubiquitin-conjugated forms of tyrosinase was performed by immunochemical detection and immunoprecipitation at 72 hours (FIG. 6). These results show that, in the cells treated with extracts of the alga *Phaeodactylum tricornutum*, tyrosinase does not accumulate in ubiquitinated form since it is rapidly degraded.

III. Examples of Cosmetic Compositions

The concentrations are expressed as weight percentages.

The extract used in the examples below is extract E2.

1. Depigmenting Cosmetic Day Cream in Emulsion-Gel Form

| | |
|---|---|
| Glycerol | 5.00% |
| Caprylic/capric/succinic triglycerides | 5.00% |
| Octyl methoxycinnamate | 1.00% |
| Dimethicone copolyol | 0.50% |
| Acrylates/C10-30 alkyl acrylate crosspolymer | 0.50% |
| Lipid extract E2 of *Phaeodactylum tricornutum* | 0.01% |
| Neutralizer | qs |
| Preserving agents, fragrances, dyes | qs |
| Water | qs 100% |

Use of the above emulsion-gel will allow people who are subjected to the more or less intense radiation of daylight, or even of direct sunlight, to maintain a light complexion and to avoid the appearance of pigmentation marks.

2. Sunlight-Protecting Fluid Cosmetic Composition (SPF 30)

| | |
|---|---|
| Volatile pentacyclomethicone | 49.00% |
| Titanium dioxide | 15.00% |
| Octyl methoxycinnamate | 7.50% |
| Glycerol | 5.00% |
| Phenyl trimethicone | 5.00% |
| Dimethicone copolyol | 3.00% |
| Polymethyl methacrylate | 2.50% |
| Butylmethoxydibenzoylmethane | 1.00% |
| Lipid extract of *Phaeodactylum tricornutum*, according to the invention | 0.1% |
| Neutralizer, fragrance, preserving agents, antioxidants | qs |
| Water | qs 100% |

This composition prevents the appearance of pigmentation marks in the case of individuals predisposed to this phenomenon during exposure to intense sunlight. It should be noted that the presence of a high concentration of sunscreen compensates for the reduction in the natural protection, which is a consequence of the decrease in the level of melanin.

3. Cosmetic Face Lotion for Lightening the Complexion

| | |
|---|---|
| Ethyl alcohol | 30.00% |
| PPG-3 myristyl ether | 5.00% |
| Glycerol | 2.00% |
| Carbomer | 0.20% |
| Polysorbate 20 | 0.20% |
| Lipid extract of *Phaeodactylum tricornutum*, according to the invention | 0.05% |
| Neutralizer, fragrance, preserving agents | qs |
| Water | qs 100% |

This complexion-lightening lotion is used after removing makeup and cleansing the skin.

4. Lightening Cosmetic Serum for the Face

| | |
|---|---|
| Water | qs 100% |
| Glycerol | 2% |
| Tetrasodium EDTA | |
| Citric Acid | qs pH 6.5 |
| Trisodium citrate | |
| Xanthan gum | 0.25% |
| Polyacrylamide, C13-14 isoparaffin, Laureth-7 | 0.5% |
| Dimethicone copolyol | 0.25% |
| Lipid extract of *Phaeodactylum tricornutum*, according to the invention | 1.0% |
| Frangrance, dye, preserving agent | qs |

One drop of this very concentrated serum composition is applied to the face generally before applying a face cream. This serum is usually used in cures of one to two weeks to obtain or maintain lightening of the complexion.

5. Cosmetic Lotion for Lightening Bodily Hair

| | |
|---|---|
| Water | qs 100% |
| Alcohol | 50% |
| Panthenyl ethyl ether | 0.5% |
| DL-α-Tocopheryl acetate | 0.2% |
| Polysorbate-60 | 1% |
| Lipid extract of *Phaeodactylum tricornutum*, according to the invention | 5.0% |
| Fragrance | 0.2% |
| Glycerol | 0.5% |
| Dye | qs |

This lotion is applied to the hairy regions to be lightened, especially the arms, for a time that is sufficient to obtain gradual lightening of the hairs.

6. Mark-Preventing Cosmetic Hand Cream-Gel

| | |
|---|---|
| Caprylic/capric diglyceryl succinate | 6% |
| Octyl octanoate | 2.5% |
| Octyl methoxycinnamate | 6% |
| Lipid extract of *Phaeodactylum tricornutum*, according to the invention | 0.01% |
| Phenyl trimethicone | 2.5% |
| Benzophenone-3 | 0.5% |
| Sodium hyaluronate | 0.05% |
| Xanthan gum | 0.2% |
| Acrylates/C10-30 alkyl acrylate copolymer | 0.5% |
| Glycerol | 2% |
| PEG-150 | 3% |
| Neutralizers, dyes, fragrance, preserving agents | qs |
| Purified water | qs 100% |

APPENDIX A

I—Buffers and Solutions Used for the Electrophoresis Gels Under Denaturing and Reducing Conditions in Batch Buffer Monomer Solution:

acrylamide/Bis-acrylamide, 30% T, 2.67% C (Biorad; ref. 161-0158)

Resolution gel buffer: Tris-HCl 1.5M pH 8.8.

18.15 g of Tris base (Sigma; T1503) per 100 ml of distilled water adjust the ph to 8.8 with 12N HCl and palmitic acid) were used, respectively, as positive and negative control to characterize the effect of the extracts of the alga *Phaeodactylum tricornutum* on the activity of tyrosinase, a limiting enzyme of melanin synthesis that governs Concentration gel buffer: Tris-HCl 0.5M pH 6.8.

6 g of tris base per 100 ml of distilled water adjust the pH to 6.8 with 12N HCl 10× migration buffer: Tris 0.25M pH 8.3, glycine 1.92M; SDS 1%

| | |
|---|---|
| Tris base | 12 g |
| Glycine (Research Organics Inc.; 5037G) | 57.6 g |
| SDS 10% (Sigma; L5750) | 40 ml |
| Distilled water to make up to | 400 ml |

These solutions are stored at 4° C.

Ammonium persulfate $(NH_4)_2S_2O_8$: (Sigma; A1433) at 10%, i.e. 100 mg/ml

Divided into aliquots and stored at −20° C.

Laemmli 2× reducing sample buffer: Tris-HCl 0.06M pH 6.8; SDS 2.3%; glycerol 10%; bromophenol blue 0.02%

| | |
|---|---|
| Concentration gel buffer Tris 0.5M pH 6.8 | 6.25 ml |
| SDS 10% | 11.50 ml |
| Glycerol | 5 ml |
| Distilled water to make up to | 50 ml |

10× bromophenol blue (saturated solution):

Place a spatula tipful of bromophenol blue in 5 ml of Laemmli 2× buffer, stir, sonicate, centrifuge and recover only the supernatant.

These solutions are stored at room temperature.

Precolored Standards— low molecular weight (Biorad; ref. 161-0305)

They are composed of:

| | |
|---|---|
| Phosphorylase B | 104 kDa |
| Bovine serum albumin | 82 kDa |
| Ovalbumin | 48.3 kDa |
| Carbonic anhydrase | 33.4 kDa |
| Soybean trypsin inhibitor | 28.3 kDa |
| Lysosyme | 19.4 kDa |

high molecular weight (Amersham; ref. RPN800) from 10 to 250 kDa

II—Gel Electrophoresis

Preparation of the Resolution Gel at 12% T

| Solutions | Volumes for 2 gels (10 ml) | Final concentrations |
|---|---|---|
| Monomer solution | 4.0 ml | 12% T; 2.7% C |
| Resolution gel buffer | 2.5 ml | 0.375M |
| SDS 10% | 100 µl | 0.1% |
| Ammonium persulfate (10%) | 50 µl | 0.05% |
| TEMED (Research Organics Inc.; 3009T) | 5 µl | |
| Distilled water | 3.4 ml | |

Preparation of the Concentration Gel at 12% T

| Solutions | Volumes for 2 gels (5 ml) | Final concentrations |
|---|---|---|
| Monomer solution | 2 ml | 12% T; 2.7% C |
| Resolution gel buffer | 1.25 ml | 0.375M |
| SDS 10% | 50 µl | 0.1% |
| Ammonium persulfate (10%) | 25 µl | 0.05% |
| TEMED (Research Organics Inc.; 3009T) | 5 µl | |
| Distilled water | 4.2 ml | |

APPENDIX B

Solutions for the Transfer and Immunodetection

Towbin Transfer Buffer:

Tris-HCl 25 mM, pH 8.3; Glycine 192 mM; 20% Methanol

| | |
|---|---|
| Tris base | 3.03 g |
| Glycine (Research Organics Inc.; 5037G) | 14.4 g |
| to be dissolved in 100 ml of distilled water | |
| Methanol | 200 ml |
| Distilled water to make up to | 1000 ml |

PBS-T Buffer

Tenfold dilution of 10×PBS (Invitrogen; 14200-067)

add thereto 0.1% Tween 20 (Sigma; P1379)

These solutions are stored at 4° C.

Ponceau Red (Sigma; P7170)

Solution at 0.1% (w/v) in a 5% acetic acid solution

APPENDIX C

Protein Assay (Biorad Kit; protein standard; ref. 500-0006)

Bradford Method

Before performing the electrophoresis, the thawed lyzates are heated at 95° C. for 10 minutes.

For the Lyzates in the Denaturing Lysis Buffer (2× Laemmli Buffer+DTT 10 mM)

The Laemmli buffer is incompatible with the reagent of the kit, and it is thus essential to remove it in order to perform the assay via this method.

In an Eppendorf tube, 500 µl of acetone are added to 5 µl of lyzate (volume to be adapted as a function of the protein concentration).

The tubes are placed at −20° C. for at least 10 minutes.

They are then centrifuged at 17 000×g for 10 minutes at 4° C.

The supernatant is removed by inversion, after evaporating off the acetone the pellet is dissolved in 50 µl of 0.1 M NaOH and the proteins are assayed via the Bradford method (tenfold dilution of the sample).

For the Lyzates in Non-Denaturing Lysis Buffer

The constituents of this lysis buffer do not interfere with the reagent of the Biorad kit at this concentration (10 µl of sample/well). Only the sample should or should not be diluted in order to be within the range and preferentially in the upper part.

Preparation of the Calibration Range:

BSA stock solution: 2 mg/ml (Sigma; A2153; 4° C.)

The range is prepared in Eppendorf tubes and may be frozen or stored at 4° C.

| Stock solutions in μg/tube final | Amount of proteins (μg/μl) | BSA (μl) | $H_2O$ (μl) |
|---|---|---|---|
| 0 | 0 | 0 | 1000 |
| 1 | 0.1 | 50 | 950 |
| 2 | 0.2 | 100 | 900 |
| 3 | 0.3 | 150 | 850 |
| 4 | 0.4 | 200 | 800 |
| 5 | 0.5 | 250 | 750 |
| 6 | 0.6 | 300 | 700 |
| 7 | 0.7 | 350 | 650 |
| 8 | 0.8 | 400 | 600 |
| 9 | 0.9 | 450 | 550 |
| 10 | 1.0 | 500 | 500 |

The reagent (Coomassie blue G250) is diluted extemporaneously fivefold (keeps for 1 hour). To a 96-well plate, add 200 μl of reagent diluted with:

10 μl of stock solution for the range

10 μl of water for the blank

10 μl of 0.1 M NaOH for the sample blank

10 μl of sample to be assayed (in triplicate or quadruplicate).

Shake the plate and allow the coloration to develop for 10 minutes.

Measure the absorbance at 595 nm. The coloration is stable for up to 40 minutes.

APPENDIX D

| Antibody | Reference | Dilution | Incubation time |
|---|---|---|---|
| Tyrosinase Ab-1 monoclonal antibody | (clone T311) Lab vision corporation. | 1/2000 | 1 hour |
| Polyclonal human Anti-20S proteasome | (ST 1053, Calbiochem) | 1/2000 | 1 hour |
| Polyclonal human Anti-26S proteasome | anti PA700, 539147, Calbiochem) | 1/2000 | 1 hour |
| Anti-monoubiquitin monoclonal | (SC-8017, Santa Cruz) | 1/5000 | 1 hour |
| Anti rabbit IgG HRP | Amersham NA9340 | 1/50000 | 1 hour |
| Anti mouse IgG HRP | Amersham NA9310 | 1/50000 | 1 hour |

What is claimed is:

1. A method for attenuating skin pigmentation marks, for lightening skin complexion, or for lightening body or head hair of a subject identified as being in need thereof comprising:

topically applying, to at least a portion of the skin or hair of said subject, a cosmetic composition comprising an extract of the algae *Phaeodactylum tricornutum* in an amount and for a time effective to attenuate the skin pigmentation marks, to lighten the skin complexion, or to lighten the hair.

2. The method of claim 1, wherein said algae extract is present at a concentration of between 0.001% and 5%, by weight of the total weight of the composition.

3. The method of claim 1, wherein said algae extract is present at a concentration of between 0.001% and 1%, by weight of the total weight of the composition.

4. The method of claim 1, wherein said algae extract contains at least 40%, by weight of the extract, of fatty acids.

5. The method of claim 1, wherein said algae extract contains at least 60%, by weight of the extract, of fatty acids.

6. The method of claim 1, wherein said algae extract is obtained from said algae by extracting with a solvent that is sufficiently apolar to extract fatty acids.

7. The method of claim 6, wherein said solvent is isopropanol, hexane, cyclohexane or heptane.

8. The method of claim 6, wherein said extraction process comprises:

at least one step of extracting with a solvent that is a $C_1$-$C_6$ alcohol, an aqueous-alcoholic mixture, a $C_2$-$C_6$ polyalcohol, ethylene glycol, a chlorinated solvent, chloroform, dichloromethane, a $C_3$-$C_6$ organic acid ester, ethyl acetate, a $C_6$-$C_{10}$ alkane, heptane, hexane, cyclohexane, a $C_5$-$C_8$ ether or diisopropyl ether, said extraction solvent being optionally basified, and any mixture thereof.

9. The method of claim 6, wherein said extraction process comprises:

extracting fatty acids from the algae with a basified aqueous-alcoholic mixture, the alcohol of the aqueous-alcoholic mixture being isopropanol, ethanol or methanol, and recovering the fatty acids in salified form in the aqueous-alcoholic mixture.

10. The method of claim 9, wherein said extraction process further comprises acidifying said aqueous-alcoholic mixture;

performing a liquid-liquid extraction using an apolar solvent;

recovering the fatty acids in an apolar phase; and

TABLE 1

| Proteasome activity at 72 hours | Control | Palmitic acid | Linoleic acid | Phaedactylum tricornutum | Control + Mg132 | Palmitic acid + Mg132 | Linoleic acid + Mg132 | Phaedactylum Tricornutum + Mg132 |
|---|---|---|---|---|---|---|---|---|
| Chymotrypsin-like pmol/min/mg | 3.8 ± 0.32 | 3 ± 0.37 | 6.3 ± 0.37 | 7 ± 0.33 | 3 ± 0.3 | 1.36 ± 0.29 | 3.5 ± 0.24 | 4.6 ± 0.25 |
| Post-glutamic hydrolase nmol/min/mg | 55.5 ± 2.4 | 54 ± 6 | 78 ± 3.6 | 88 ± 6.8 | 42 ± 5 | 44 ± 2.2 | 59 ± 5.5 | 61 ± 7 |
| Trypsin-like pmol/min/mg | 1915 ± 171 | 1998 ± 261 | 2848 ± 424 | 2054 ± 258 | 627 ± 282 | 456 ± 169 | 569 ± 261 | 456 ± 248 |

removing the said apolar solvent to obtain said extract in the form of an oil.

11. The method of claim 10, wherein said apolar solvent is heptane, hexane or cyclohexane.

12. The method of claim 1, wherein said algae extract is obtained by extraction using supercritical $CO_2$.

* * * * *

UNITED STATES PATENT AND TRADEMARK OFFICE

CERTIFICATE OF CORRECTION

PATENT NO. : 8,372,408 B2
APPLICATION NO. : 12/530266
DATED : February 12, 2013
INVENTOR(S) : Nizard et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 548 days.

Signed and Sealed this
First Day of September, 2015

Michelle K. Lee
*Director of the United States Patent and Trademark Office*